US005395365A

United States Patent [19]

Weiler et al.

[11] Patent Number: 5,395,365

[45] Date of Patent: Mar. 7, 1995

[54] CONTAINER WITH PIERCEABLE AND/OR COLLAPSIBLE FEATURES

[75] Inventors: Gerhard H. Weiler, South Barrington; Henry Komendowski, Des Plaines, both of Ill.

[73] Assignee: Automatic Liquid Packaging, Inc., Woodstock, Ill.

[21] Appl. No.: 34,727

[22] Filed: Mar. 22, 1993

[51] Int. Cl.[6] .......................... A61B 19/00; A61M 5/32

[52] U.S. Cl. .......................... 604/415; 604/403; 604/408; 604/905; 128/DIG. 24; 206/505; 206/514; 206/515; 215/230; 215/247; 220/253; 220/258

[58] Field of Search .......................... 128/912, D26, D24; 604/56, 82–92, 148, 161, 200–205, 213, 240–247, 249, 256, 259, 323, 403, 411, 414, 415, 905, 408–409; 215/230, 247, 321; 220/213, 253, 256–258; 206/505, 514, 515, 517

[56] References Cited

U.S. PATENT DOCUMENTS

| | | | |
|---|---|---|---|
| D 257,287 | 10/1980 | Pagels . | |
| 2,494,456 | 1/1950 | Still | 604/416 |
| 2,950,029 | 8/1960 | Winstead | 206/517 |
| 3,343,541 | 9/1967 | Bellamy, Jr. | 604/408 |
| 3,460,702 | 8/1969 | Andrews | 215/247 |
| 3,682,315 | 8/1972 | Haller | 604/415 |
| 4,178,976 | 12/1979 | Weiler et al. . | |
| 4,207,990 | 6/1980 | Weiler et al. . | |
| 4,239,726 | 12/1980 | Weiler et al. . | |
| 4,519,513 | 5/1985 | Weiler et al. . | |
| 4,553,971 | 11/1985 | Ashley et al. | 604/415 |
| 4,863,453 | 9/1989 | Berger et al. | 604/415 |
| 5,232,109 | 8/1993 | Tirrell et al. | 604/415 |

FOREIGN PATENT DOCUMENTS

| | | | |
|---|---|---|---|
| 472091 | 9/1936 | United Kingdom | 215/247 |

*Primary Examiner*—Randall L. Green
*Assistant Examiner*—P. Zuttarelli
*Attorney, Agent, or Firm*—Olson & Hierl, Ltd.

[57] ABSTRACT

A hermetically sealed package is provided for the administration of a solution or other liquid to a patient. The package includes a blow molded container, cap, and releasable cover. The cap accommodates piercing of the cap and container with a draining spike. The cap has one or more self-closing seals or liners and can be disposed on the container so as to permit penetration of the cap and container by a piercing spike without contacting the parting line of the molded container. The cap includes a special structure for guiding the spike at the initiation of the piercing process, and the cap has an improved structure for sealingly engaging the spike upon insertion. As the container is drained, one of the container walls collapses toward the other to facilitate the draining process and provide a convenient shape for subsequent handling and storage.

18 Claims, 5 Drawing Sheets

CONTAINER WITH PIERCEABLE AND/OR COLLAPSIBLE FEATURES

TECHNICAL FIELD

This invention relates to a package which includes at least a container portion from which fluid contents can be dispensed. The package is particularly suitable for use with, or as part of, an administration or delivery system for supplying a parenteral solution or other liquid to a patient.

BACKGROUND OF THE INVENTION

Parenteral solutions or other liquids may be conventionally administered to a patient from a container elevated above the patient and connected to the patient through a suitable fluid-transfer system. Such a fluid-transfer system may include a tube with a spike, cannula, or connector on one end for communication with the container interior and a hollow needle or cannula on the other end for being connected, directly or indirectly, to the patient.

One type of conventional container is blow molded from thermoplastic material, filled with the desired substance, and then hermetically sealed. Such a container is typically provided with a hanging loop on the top and a membrane on the bottom which can be pierced by a draining spike or cannula. Such containers may be provided in a generally non-collapsible form, and examples are disclosed in the U.S. Pat. Nos. 4,178,976, 4,239,726, and 4,519,513. A collapsible container suitable for medical fluids is disclosed in U.S. Pat. No. Des. 257,287.

When a container is pierced and drained through a spike, cannula, or the like, it is desirable to effect maximum drainage of the fluid contents from the container. Accordingly, it would be beneficial to provide an improved design which effectively promotes drainage of the container.

Further, in order to facilitate handling and storage of empty (drained) containers, it would be desirable to provide a container that, when empty or substantially empty, has a relatively compact configuration which accommodates such handling and storage.

Some types of hermetically sealed containers typically employ a substantially rigid, thermoplastic membrane which is adapted to be pierced by a cannula or draining spike. In such containers, the membrane size and shape can make the piercing operation difficult. There is a risk that the spike or cannula may slip off of the membrane and accidentally puncture the skin of the person who is attempting to establish the connection with the container.

Accordingly, it would be desirable to provide an improved container membrane structure for guiding the cannula, hollow needle, piercing spike, or the like during penetration of the container membrane. It would also be advantageous if such an improved membrane structure could be provided with a configuration for eliminating or minimizing the tendency of the hollow piercing instrument to "core" the membrane material which could form a plug blocking the flow through the instrument.

In some situations, it may be desirable to provide a pierceable cap or overcap with a self-sealing liner or seal that is located over the container membrane. This type of seal or liner accommodates penetration by a cannula or needle and permits subsequent removal of the cannula or needle without leaking. Such a system would permit repeated making or breaking of connections with the container. Such a system would also permit the use of a syringe needle or cannula for injecting additives or liquid agents into the container.

It would be beneficial in some applications to provide an improved, pierceable cap or overcap system with more than one site for accommodating penetration by a draining spike, cannula, syringe needle, or the like. It would be advantageous if such plural sites could each be of the self-sealing type to permit removal of the penetrating instrument without causing the container contents to subsequently leak from the container. Further, it would be beneficial if an improved penetration site in such a cap could function to provide increased forces for holding or gripping the penetrating instrument and for eliminating or minimizing leakage around the penetrating instrument.

Further, in a cap having a plurality of self-sealing penetration sites, it would be desirable to provide an overcap structure that would prevent a large draining spike from being inadvertently inserted into a penetration site intended for a smaller diameter needle or cannula.

Additionally, it would be advantageous if such a cap could optionally include exterior sealing means for sealing the penetration site or sites until the container is ready for use so as to provide a sterile and aseptic package. Such a sealing means should preferably be easily removable so as to facilitate use of the package.

Further, it would be desirable to provide a package design that would accommodate the mounting of a penetrable cap or overcap on a molded container in a way that would position the penetration region of the cap away from the molded container parting line. This would eliminate or minimize the problems that can be encountered when a piercing spike, cannula, or needle is forced against a region of the molded container where a ridge of material along the container parting line tends to inhibit penetration of the spike, cannula, or needle.

Finally, it would be beneficial if such an improved package could be readily manufactured by conventional, and relatively inexpensive, processes.

The present invention can be incorporated in a package design having many of the aforementioned benefits and features.

SUMMARY OF THE INVENTION

The present invention provides a novel container, as well as a novel package structure which includes such a container, that is especially suitable for dispensing parenteral solutions or other liquids.

According to one aspect of the present invention, a pierceable container is provided with a hollow body portion which defines an access port and which is suitable for containing a substance to be drained. A sealing wall is coextensive with, and seals, the access port. The sealing wall includes a pierceable membrane and defines guide surfaces that converge toward the pierceable membrane and that define a recess for receiving a piercing spike (e.g., a hollow cannula, hollow needle of a syringe, or the like).

Another aspect of the invention relates to a pierceable package which includes a container and a cap or overcap for the container. The container has an access port defined by a boss unitary with the container and sealed by a unitary pierceable membrane. The cap is secured to the boss over the membrane, and the cap includes a pierceable, resilient, self-sealing seal or liner juxtaposed over the container membrane. The self-sealing seal or liner includes an exposed target surface and a deformable, interior surface facing toward the pierceable membrane. The deformable, interior surface defines a recess aligned with the exposed target surface and provides an inwardly enlarging passageway. This supplies increased resistance against removal of a piercing spike when the spike is inserted through the target surface to extend inwardly beyond the recess in the deformable interior surface and penetrate the container membrane.

Another aspect of the present invention relates to a system for mounting an overcap or cap on a container that is molded in a split mold and has a parting line delineating opposing portions of the molded container. The container has an access port thereto defined by a boss and sealed by a pierceable membrane across which the parting line extends. The cap is attached to the boss over the membrane and includes a resilient, self-sealing liner having an exposed, pierceable, target portion over the container membrane.

The container boss and cap have cooperating orientation means for placement of the cap on the container boss in a predetermined orientation relative to one another and for positioning the liner target portion away from the parting line on the pierceable membrane. Thus, when the cap is pierced with a spike or similar piercing device, the spike can be directed through the exposed target portion of the cap liner and through an underlying a portion of the container membrane from which the parting line is absent.

In accordance with another aspect of the invention, a pierceable package includes a molded container having an access port thereto defined by a boss and sealed by a pierceable membrane. A cap or overcap is mounted on the boss over the membrane. The cap includes a pierceable, resilient, self-closing seal or liner in registry over an area of the container membrane. The cap includes a housing that is substantially more rigid than the seal and that encloses the seal while exposing at least one pierceable target region of the seal. The housing is secured to the container boss to retain the seal in position and includes an annular, raised rim around the seal target region. A removable cover is releaseably sealed to the housing rim over the self-closing seal to isolate the seal target region from the ambient atmosphere.

The invention may be employed in a molded, filled, and collapsible container from which a substance can be drained under the influence of gravity. The container includes a molded body portion having a sump at one end of the body portion that communicates with the interior of the body portion. The sump includes a closure means for accommodating draining of the substance therethrough. The body portion defines a pair of opposed walls joined around at least a portion of the periphery of the body. One of the walls is structurally less stiff than the other wall and collapses inwardly toward the other wall in a generally nesting relationship when the substance is drained from the container. This helps insure maximum drainage of the container contents and also facilitates handling and storage of the empty containers.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

DESCRIPTION OF THE PREFERRED EMBODIMENTS

Figure 1:
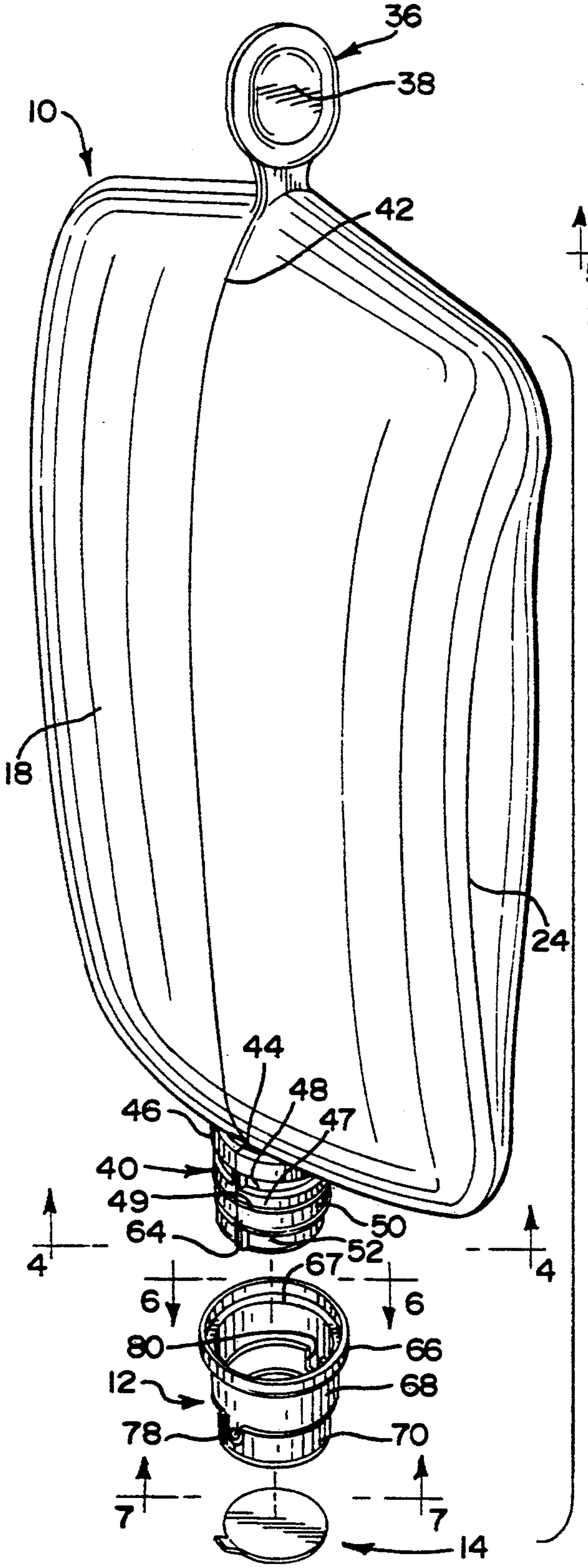
FIG. 1 is an exploded perspective view of a first embodiment of a package according to the present invention.

The present invention is particularly suitable for facilitating the administration of a parenteral solution or other liquid to a patient. According to a preferred form of the invention, a package comprising a container, cap, and releasable cover seal can be provided as a sterile unit with a parenteral solution in the container.

The cap accommodates repeated piercing of the cap and container with a draining spike and/or syringe needle. The cap can be provided with one or more self-closing seals or liners and can be disposed on the container so as to permit penetration of the cap and container by a piercing spike without contacting the parting line of the molded container.

The cap can include a special structure for guiding the spike at the initiation of the piercing process, and the cap can be provided with an improved structure for sealingly engaging the spike upon insertion. As the container is drained, one of the container walls collapses toward the other wall to facilitate the draining process and to provide a convenient shape for subsequent handling and storage.

While this invention is susceptible of embodiment in many different forms, this specification and the accompanying drawings disclose only some specific forms as examples of the invention. The invention is not intended to be limited to the embodiments so described, and the scope of the invention will be pointed out in the appended claims.

For ease of description, the container, cap and assembled package of this invention are described in the normal (inverted) dispensing position, and terms such as upper, lower, horizontal, etc., are used with reference to this position. It will be understood, however, that the package of this invention may be stored, transported, and sold in an orientation other than the position described.

Preferably, the container included in this package is initially molded and filled as a unitary, hermetically sealed structure (in an orientation inverted from that shown in FIGS. 1 and 13) generally utilizing form, fill and seal techniques and apparatus described in U.S. Pat. No. 4,178,976 to Weiler et at. The package of this invention may be fabricated and assembled with automatic molding apparatus and other mechanisms, the details of which, although not fully illustrated or described, will be apparent to those having skill in the art and an understanding of the necessary functions of such apparatus and mechanisms. The detailed descriptions of such apparatus and mechanisms are not necessary to an understanding of the invention and are not herein presented because such apparatus and mechanisms form no part of the present invention.

The present invention permits a variety of thermoplastic materials (e.g., low density polyethylene, polyproylene, polyvinylchloride, ethylene vinyl acetate, etc.) to be molded with a split mold process to provide a hermetically sealed dispensing container from which the contents can be discharged by piercing a membrane with a piercing device such as a draining spike, cannula, or the like. Also, agents can be injected into the container through the membrane by means of a syringe.

A first type of a container, cap, and removable cover or seal which constitute a package embodying aspects of the present invention are illustrated in FIGS. 1–14. The container is designated generally by the reference numeral 10, the cap by the references numeral 12, and the removable cover by reference numeral 14.

Figure 2:
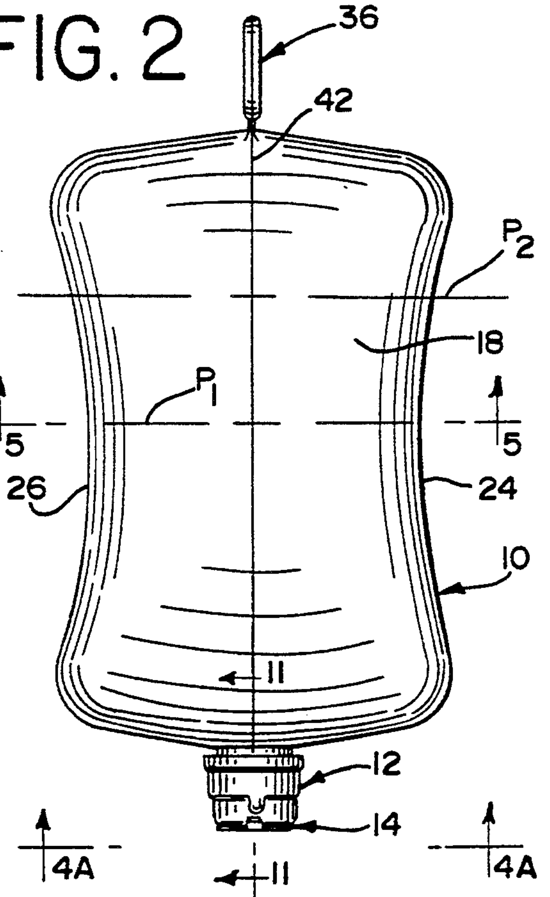
FIG. 2 is a reduced front elevational view of the assembled package.
Figure 3:
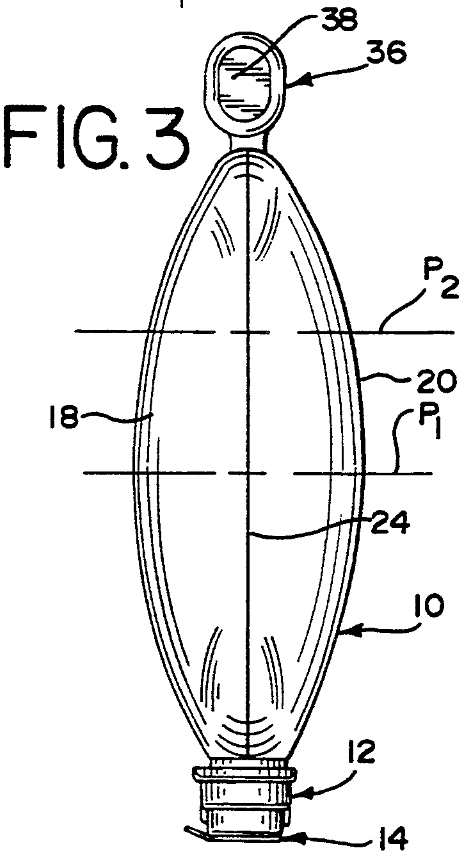
FIG. 3 is a right side elevational view of the package shown in FIG. 2.
Figure 4:
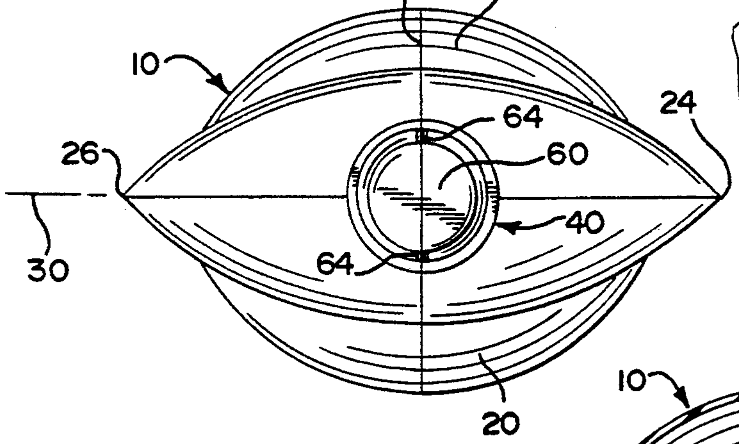
FIG. 4 is a slightly enlarged, bottom plan view of the container portion of the package taken generally along the plane 4—4 in FIG. 1.
Figure 5:
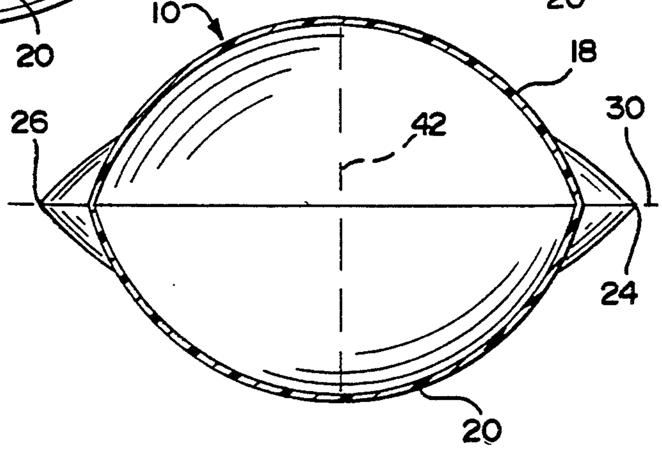
FIG. 5 is an enlarged, cross-sectional view taken generally along the plane 5—5 in FIG. 2.
Figure 6:
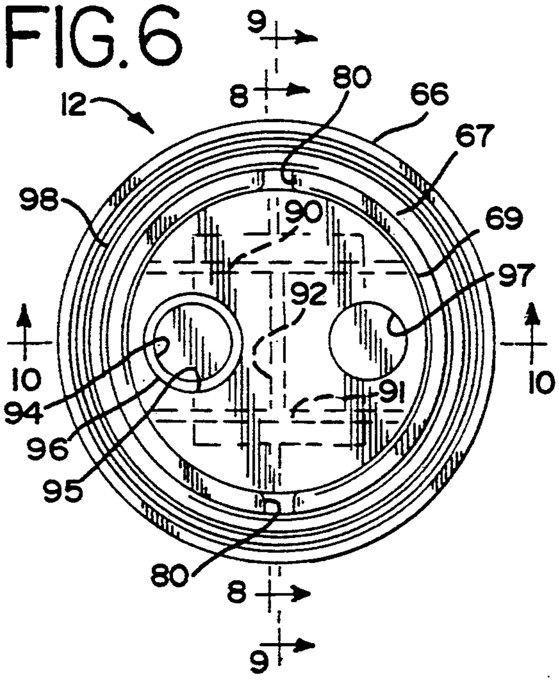
FIG. 6 is an enlarged plan view of the package cap taken generally along the plane 6—6 in FIG. 1.

As can be seen in FIGS. 1–5, the preferred form of the container 10 has a front wall 18 and a rear wall 20 which each bulge outwardly. When the container 10 is filled, the walls 18 and 20 each define a generally outwardly convex curve (when the container 10 is viewed in side elevation as shown in FIG. 3). Further, a transverse cross section taken at any vertical elevation through the filled container 10 (e.g., along plane $P_1$ as identified in FIG. 2 for the cross section as shown in FIG. 5) is defined by an outwardly convex configuration for both the front wall 18 and rear wall 20. The maximum distance between the front wall 18 and rear wall 20 occurs generally at the vertical midpoint of the body portion of the container 10 as can be seen in FIG. 3.

The side edge regions of the container 10 curve inwardly from the top and bottom ends toward the vertical midpoint of the container to define oppositely facing concave side edges 24 and 26 where the walls 18 and 20 are joined together (FIG. 2).

In the preferred form of the container 10, the container body portion is generally symmetrical relative to selected central reference planes. The curvatures of the front and rear walls 18 and 20 and the curvatures of the side edges 24 and 26! have special orientations relative to vertical planes passing through the center of the symmetrical body portion of the container 10. In particular, the side edges 24 and 26 preferably lie along a central folding plane 30 (FIG. 5) which passes through the central vertical axis of the body portion of the container 10.

Further, the arcuate lengths of the front wall 18 and rear wall 20 (as measured between the side edges 24 and 26) are preferably established according to a unique criterion relative to the vertical height of the body portion of the container 10. This criterion can be described with reference to FIG. 5 which shows the transverse cross section defined along a first selected plane $p_1$ which is perpendicular to the longitudinal or vertical axis of the body portion of the container 10. The length (arc length) of the front wall 18 along the transverse plane $P_1$ is equal to the length (arc length) of the rear wall 20 along the plane $P_1$. This relationship is the same at any other transverse plane, such as plane $P_2$ (FIG. 2), which is parallel to, but vertically spaced from, the plane $P_1$.

Figure 12:
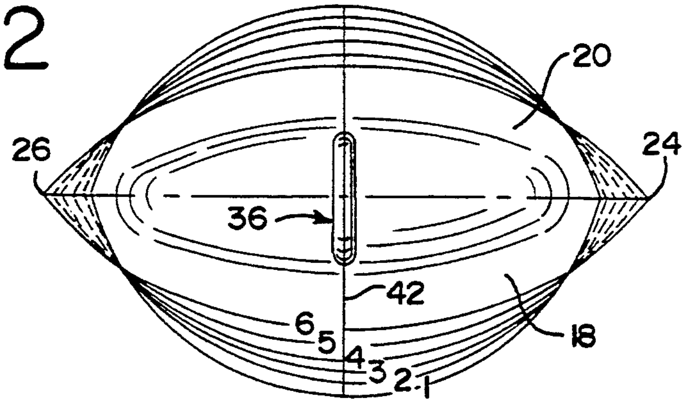
FIG. 12 is a top plan view of the package.

Further, the length of the front wall 18 along plane $P_2$ is equal to the length of the front wall 18 along the plane $P_1$ or along any other parallel, transverse plane within the vertical portion of the container defined between the concave portions of the side edges 24 and 26. In other words, the locus of the intersection of each wall 18 and 20 with a first selected plane defining a transverse cross section of the container 10 has a length equal to the length of the locus of the intersection of the wall with a second selected plane parallel to, and spaced from, the first selected plane wherein the parallel planes are longitudinally located to intersect the concave side edge regions. This is illustrated in FIG. 12 which shows the loci of the intersections of six, parallel, transverse, cross-sectional planes with the container walls. The intersection loci are numbered 1, 2, 3, 4, 5, and 6, and each intersection locus has a length equal to any of the other intersection loci.

Figure 14:
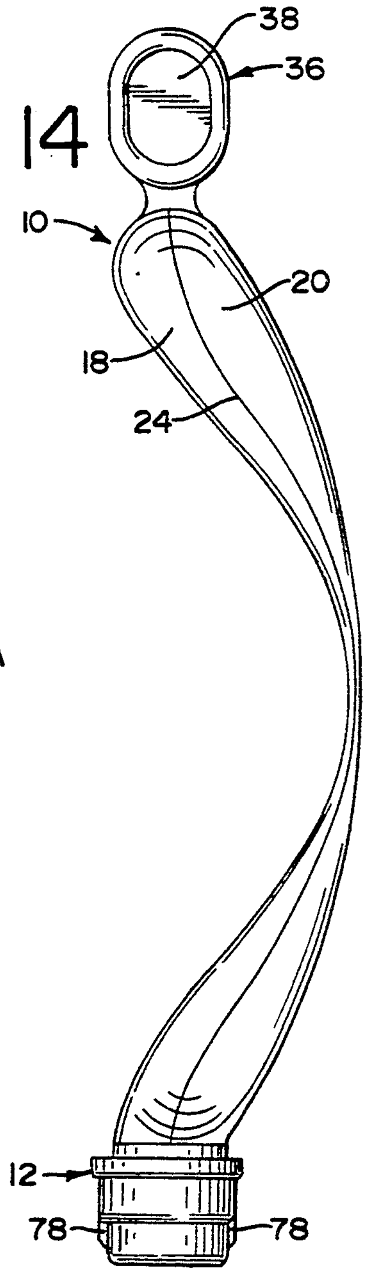
FIG. 14 is a right side elevational view of the container and cap shown in FIG. 13, but with the body of the container in a collapsed condition subsequent to drainage of the fluid contents from the container.

In order to facilitate draining of the container 10, and in order to better accommodate handling and storage of the container after it has been drained (by means described in detail hereinafter), the structure of the container 10 is adapted to collapse in a substantially predetermined manner as illustrated in FIG. 14. In particular, the front wall 18 collapses inwardly toward the rear wall 24. This is achieved by forming the container 10 so that the front wall 18 is structurally less stiff than the rear wall 20. As a result, the front wall 18 can collapse to form a generally nesting relationship with the rear wall 20 as the container is drained.

Figure 13:
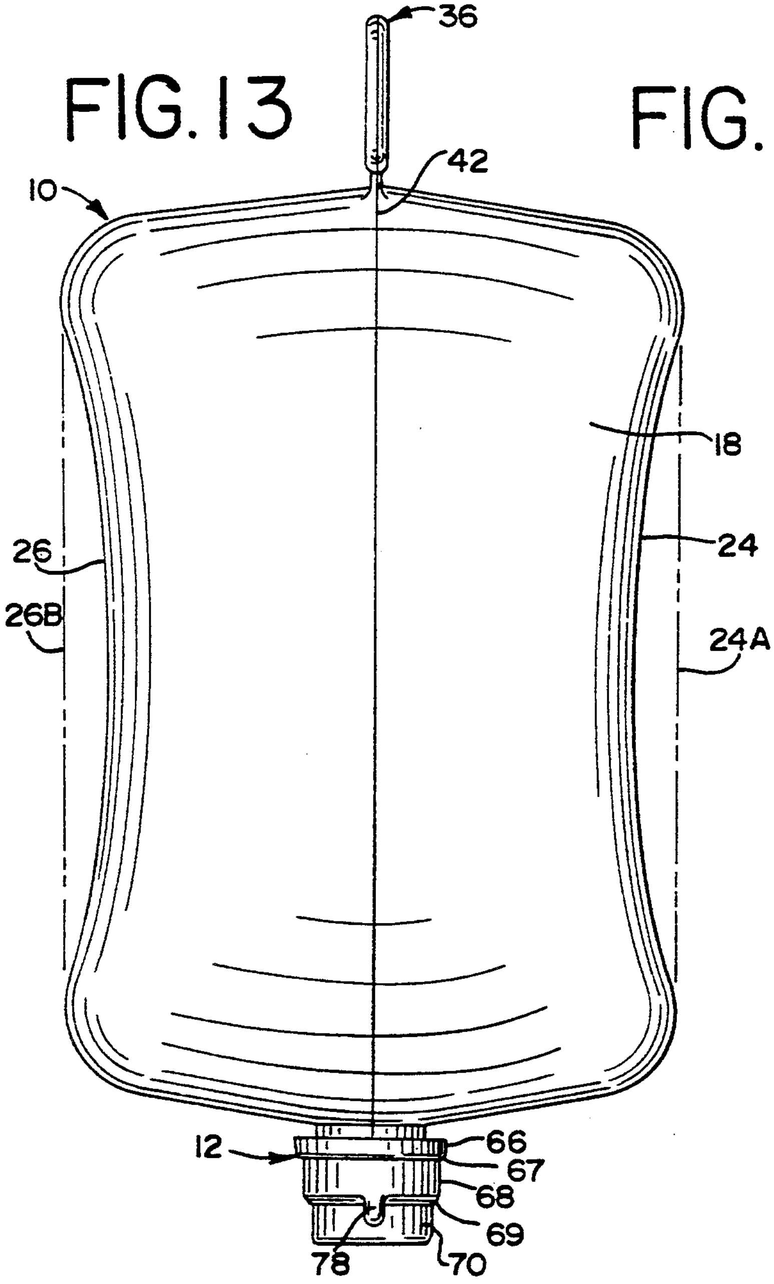
FIG. 13 is a view similar to FIG. 2, but with the releasable seal removed from the bottom of the cap.

When the container is substantially fully collapsed, as illustrated in FIG. 14, then the side edges or regions 24 and 26 are displaced laterally outwardly, and this is indicated in FIG. 13 for edge 24 by the dashed line 24A and for edge 26 by the dashed line 26B. In the collapsed condition (FIG. 14), the top and bottom regions of the container define residual, non-collapsed volumes. However, for a contemplated 1,000 ml. size polypropylene container, most of the liquid can be drained from such a container with a standard draining spike if the container is initially filled with liquid and less than about 30 cc. of air or other gas at atmospheric pressure and if the container's approximate dimensions are 8 inches long, 5 inches wide and 3 inches thick.

The difference in stiffness between the front and rear walls can be effected by forming the front wall 18 so that it is thinner than the rear wall 20. For a typical contemplated commercial container 10, the difference in wall thickness is relatively small, and the difference in not apparent in the cross-sectional view shown in FIG. 5. The thickness of the front wall 18 and rear wall 20 will depend, of course, upon, inter alia, the size of the container and the material from which the container is made.

Rather than making one of the walls 18 or 20 thinner relative to the other, the difference in stiffness of the walls can be effected by other means. For example, rigidifying gussets (not illustrated) or other structures can be provided in one of the walls to make it more stiff compared to the other wall. In any event, the wall structure and thickness are preferably carefully controlled, as with computer aided manufacturing techniques, to insure that the desired dimensions are maintained so that the container collapses in the intended manner during draining of the container. Further, the thickness of the folding region at the juncture of the front and rear walls along the side edge regions 24 and 26 on the plane 30 (FIG. 5) is controlled, and this can be effected with deep draw techniques.

The container 10 also includes a neck or boss 40 defining a drain sump on the bottom, and the container includes a hanging loop or ring 36 on the top. The hanger 36 is typically molded with an interior web 38 which is connected via a conventional, reduced-thickness, a frangible portion of material, and the web 38 can be knocked free of the ring 36 to define an aperture for receiving a support hook or hanger (not shown).

Using blow molding form, fill, and seal techniques, such as described in the U.S. Pat. No. 4,178,976 to Weiler et al., the container 10 is formed so that the container is initially molded in an inverted position from that shown in FIGS. 1 and 13. That is, the mold halves are configured so that the container is initially molded with the boss 40 at the top and the hanging ring 36 at the bottom.

The container 10 is made by a parison blow molding procedure wherein the hanging ring 36 and body portion are formed first. The body portion is then charged with the desired liquid fill and thereafter sealed by the formation of a closure means defined by the neck or boss 40. Preferably, the blow molding, filling, and sealing operations are carried out automatically under sterile conditions using procedures known to the art.

The container body portion, ring 36, and boss 40 are preferably blow molded, filled, and sealed in a split mold wherein the mold halves define a parting line delineating opposing portions of the molded container. The parting line is defined, at least in part, by a very low, narrow ridge of material, and the parting line is generally designated by the reference numeral 42 in FIGS. 1–5, 12, and 13. The parting line 42 extends completely around the exterior surface of the container 10. In the preferred embodiment, the container 10 is symmetrical about a central, vertical plane of symmetry, and the parting line 42 lies on the vertical plane of symmetry.

The neck structure or boss 40 is typically molded by a pair of sealing mold halves which form the exterior configuration of the boss 40, including the continuation of the parting line 42 around the exterior of the boss 40. During the molding process, after the container body is blow-molded in the main mold halves, the container is filled with the desired substance via a top insertion nozzle on a filling assembly. Upon withdrawal of the filling assembly, the sealing mold halves are closed at the parting line 42 to complete the molding of the container boss 40 and hermetically seal the contents in the container.

Figure 11:
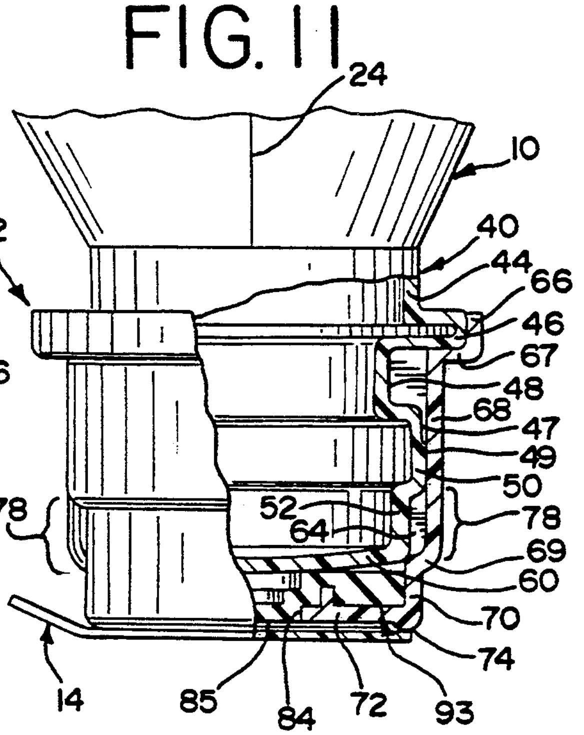
FIG. 11 is an enlarged, fragmentary, partial, cross-sectional view taken generally along the plane 11—11 in FIG. 2.

As illustrated in FIGS. 1 and 11, the boss 40 includes a generally cylindrical neck portion 44, a rim 46, a groove 48, a first, cylindrical, side wall portion 47, a very narrow annular shoulder 49, a second, cylindrical, side wall portion 50, a reduced diameter, cylindrical, side wall portion 52, and a slightly convex, sealing end wall or membrane 60. The membrane 60 is adapted to be pierced by a suitable piercing instrument or device, such as a piercing spike, cannula, or the like.

The boss 40 also includes a pair of outwardly projecting orientation means in the form of lugs 64 (FIGS. 1, 4, and 11). The lugs are 180° apart and lie on the parting plane along the parting line 42. Each lug 64 projects outwardly from the reduced diameter, cylindrical, side wall portion 52 and extends from the end of the second, cylindrical side wall portion 50 to the outer periphery of the pierceable membrane end wall 60.

The overcap or cap 12 is adapted to be secured over the container boss 40 in a specific orientation and functions to accommodate piercing of the boss membrane 60 by a draining spike or syringe needle and to automati7 cally reseal the package upon removal of the spike or needle. The cap 12 includes a housing that is made of a relatively rigid, molded, thermoplastic polymer, such as ethylene vinyl acetate, or the like. If desired, the polymer can be pigmented to contrast the appearance thereof in relation to a preferred, substantially transparent or translucent appearance of the container 10.

Figure 8:
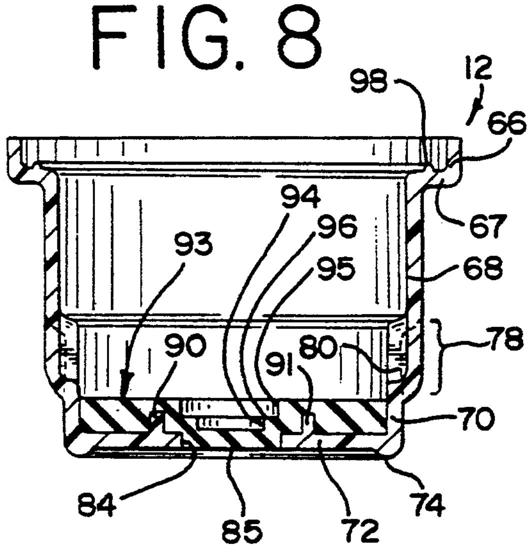
FIG. 8 is a cross-sectional view taken generally through the larger diameter target portion of the cap along the planes 8—8 in FIG. 6.
Figure 9:
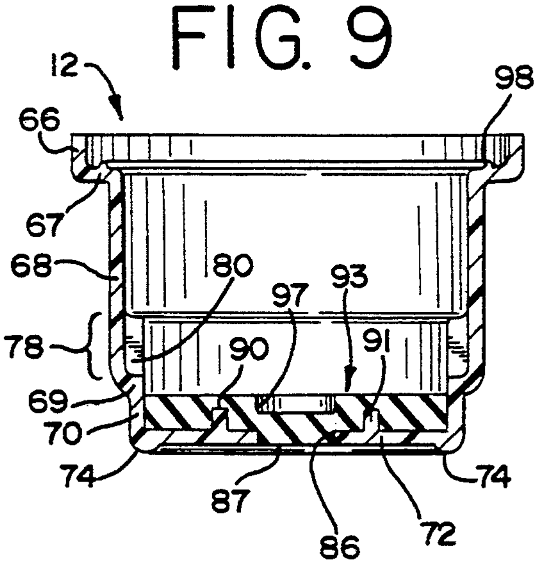
FIG. 9 is a cross-sectional view taken generally through the smaller diameter target portion of the cap along the planes 9—9 in FIG. 6.
Figure 10:
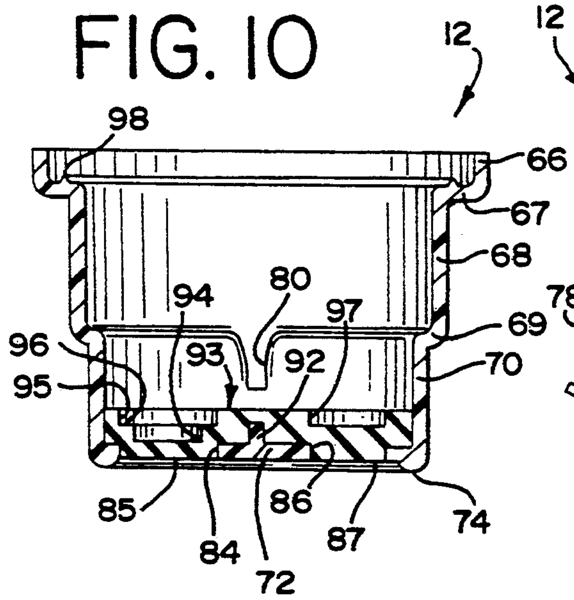
FIG. 10 is a cross-sectional view taken generally along the plane 10—10 in FIG. 6.

As illustrated in FIGS. 8–11, the housing of the cap 12 includes an outer skirt 66 for engaging the boss rim 46 (FIG. 11). The cap 12 further includes a first cylindrical portion 68 joined to the skirt 66 with an annular wall or flange 67. A reduced diameter, second cylindrical portion 70 is joined via a shoulder region 69 to the first cylindrical portion 68. The cap 12 has a generally transverse end wall 72 extending inwardly from the cylindrical wall portion 70. Preferably, as can be seen in FIGS. 8–10, the cap 12 includes an annular rim 74 projecting outwardly from the end of the cylindrical wall portion 70 around the end wall 72. The end wall 72 may thus be characterized as being recessed relative to the rim 74.

The cap 12 has a pair of convex formations 78 which bulge outwardly from the cylindrical wall portion 70. The formations 78 are located 180° apart and each defines an interior recess 80 (FIGS. 1, 6, 8, 9, and 10). When the cap 12 is installed on the container boss 40, each recess 80 is adapted to receive one of the container boss lugs 64. Each recess 80 thus functions as a cooperating orientation means for orienting the cap 12 relative to the container boss 40. Because the container boss lugs 64 are 180° apart and the cap recesses 80 are 180° apart, the cap can be installed on the container in two different orientations. However, in the preferred embodiment illustrated, the container boss 40 is symmetric about the parting line 42 on which the lugs 64 lie, and it makes no difference in which of the two positions the cap 12 is installed on the container.

Figure 4A:
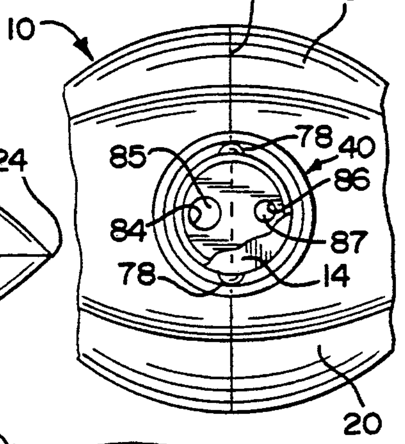
FIG. 4A is an enlarged, fragmentary, bottom plan view of the assembled package taken along the plane 4A—4A in FIG. 2.

The placement of the cap 12 in either of the two positions on the container boss 40 is important with respect to positioning the cap end wall features relative to the container boss parting line 42 which extends across the container boss end wall 60 (FIGS. 4 and 4A). As explained in detail hereinafter, the cap 12 defines target areas or regions through which a piercing spike or cannula is inserted for piercing the container boss end wall membrane 60, and it is desirable to insure that the spike passes through the cap and into a portion of the end wall membrane 60 that does not contain the ridge of material defined by the parting line 42. The cap target areas through which the spike is inserted are located, by virtue of the predetermined orientation of the cap 12 on the container, on one side or the other of the parting line 42 which extends across the center of the container boss end wall membrane 60.

Figure 7:
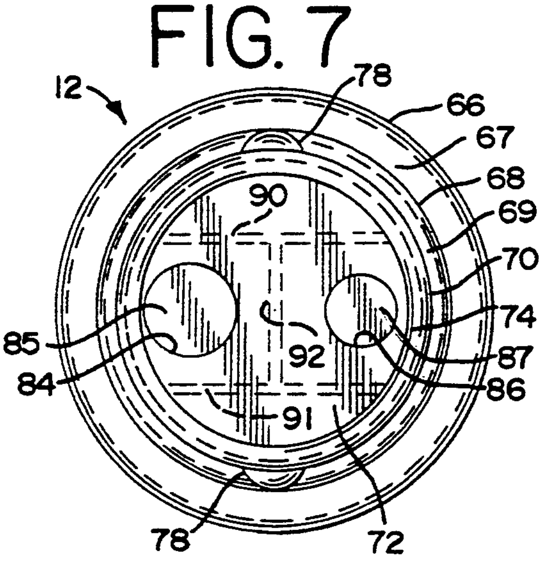
FIG. 7 is an enlarged bottom plan view of the package cap taken generally along the plane 7—7 in FIG. 1.

The cap target areas are defined in the cap end wall 72 by a pair of target apertures: a first, circular, target aperture 84 and a second, circular, target aperture 86 (FIG. 7). The diameter of the first, circular, target aperture 84 is larger than the diameter of the second, circular, target aperture 86. The larger diameter aperture 84 accommodates insertion of a large diameter draining spike, and the smaller diameter aperture 86 accommodates penetration by a smaller cannula or syringe needle. Owing to the difference in diameters, the larger draining spike cannot be inadvertently inserted into the smaller diameter aperture 86. Although two different size apertures are illustrated, it will be appreciated that only one aperture, or more than two apertures, could be provided. Further, the apertures may have the same diameter.

Preferably, the inside surface of the cap end wall 72 has three, rigidifying ribs 90, 91, and 92 which together define an H-shaped configuration (turned sideways as viewed in FIG. 7). The rib 92, forming the cross bar of the H, projects inwardly from the cap end wall 72 between the two apertures 84 and 86. As illustrated in FIGS. 7, 8, and 9, the rib 90 extends inwardly from the cap end wall 72 along one side of the apertures 84 and 86, and the rib 91 extends inwardly from the cap end wall 72 along the other side of the apertures 84 and 86.

The cap 12 includes a novel structure for permitting a draining spike or syringe needle to be removed from piercing engagement with the container end wall membrane 60 without the container contents leaking from the container after removal of the spike or needle. To this end, the cap 12 includes a self-closing seal or liner 93 which is disposed inside the cap against the cap end wall 72. The liner 93 presents a first, exposed, circular, target portion or region 85 (FIG. 7) in the large aperture 84 and presents a second, exposed, circular target portion or region 87 in the second target aperture 86 (FIG. 7). The liner or seal material at each target region 85 and 87 defines a pierceable seal at the apertures 84 and 86, respectively.

The liner or seal 93 need not extend over the entire inner surface of the cap end wall 72. However, in the preferred embodiment, the liner 93 is conveniently formed so as to be generally coextensive with the end wall 72. The seal 93 is preferably fabricated from a resilient material which can be a synthetic elastomer, such as a thermoplastic polymer rubber or other suitable material. The seal material is preferably compatible with the substance that is sealed within the container 10. In some applications, it may be desirable to provide a seal material that can be sterilized by means of radiation, steam, ethylene oxide, or by other means.

The seal 93 can be pierced, punctured, or penetrated by a draining spike, cannula, syringe needle, or the like. Withdrawal of the penetrating instrument allows the residual bias or inherent resiliency of the seal material to close the penetration site. This prevents ingress of unwanted contaminates and prevents egress of any substance remaining in the container 10.

As used in the specification and in the appended claims, the terms "seal" or "liner" will be used interchangeably with the understanding that the seal 93 functions to (1) seal closed the target apertures 84 and 86 in the absence of a penetrating member, (2) seal around the exterior of the penetrating member that is inserted through the seal 93, and (3) re-close or re-seal the penetration site upon withdrawal of the penetrating member from the seal.

In a preferred form, the seal or liner 93 provides an enhanced sealing function and gripping function relative to a penetrating member, such as a spike, cannula, or needle. To this end, the seal interior surface (which faces toward the container boss pierceable membrane 60) defines a first, cylindrical recess 94 which is oriented to be concentric with the cap end wall aperture 84 and with the exposed, seal target surface area 85 within that aperture 84. The seal further defines a larger diameter, second, cylindrical recess 95 that is coaxial with the first recess 94 so as to provide an annular shoulder 96 around the first recess 94. The structure of the smaller diameter recess 94 and larger diameter recess 96 may be characterized as providing an inwardly enlarging passageway in the portion of the deformable interior surface of the seal 93 which is aligned with the exposed, seal target surface area 85 in the cap end wall aperture 84. This structure provides increased gripping forces for retaining a draining spike n the cap after the tip of the spike has pierced the container boss membrane 60 and the container contents are being drained through the spike. The sealing around the spike is also enhanced.

If desired, a similar recess structure may be provided in alignment with the smaller aperture 86. In the preferred embodiment illustrated, only one recess 97 is employed for providing enhanced sealing of a syringe needle that is temporarily inserted through the aperture 86, seal 93, and container boss end wall 60 and that can be used for injecting an additive agent or other substance or for withdrawing a small quantity of the container contents.

The cap 12 is preferably injection molded, and co-injection techniques may be employed, including the rotary method, the core back method, and the core holder slide method. In such methods, the cap housing is formed with a primary injection of thermoplastic material, and the resilient seal 93 is formed with a secondary injection of suitable material. In a presently contemplated embodiment, the depth of each recess 85, 87, and 97 in the seal 93 is between about 0.050inch and about 0.060 inch.

Figure 21:
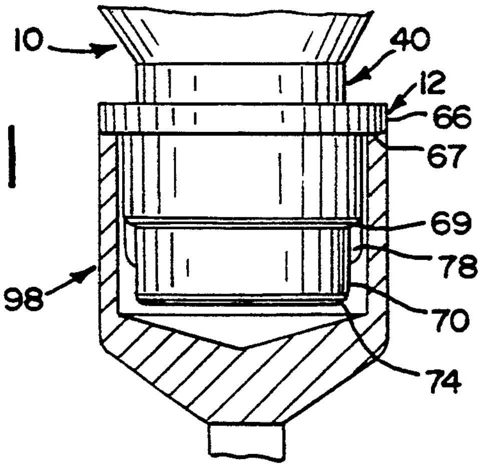
FIG. 21 is a fragmentary, side elevational view of a container and cap shown in FIG. 1 being assembled with an ultrasonic welding horn shown diagrammatically and partially in cross section.

The cap 12 may be mounted and secured to the container 40 by suitable conventional or special means. In one presently contemplated embodiment, the cap 12 is ultrasonically welded to the container boss 40 as illustrated in FIG. 21. To this end, the cap 12 is initially oriented so as to align the convex formations 78 (which define the interior recesses 80) with the container boss orientation lugs 64. The cap 12 is then pushed onto the boss so that the cap annular wall or flange 67 (FIG. 11) bears against the surface of the container boss rim 46. A hollow, ultrasonic welding horn 98 is positioned over the installed cap 12 as illustrated in FIG. 21, and the horn 98 is operated to effect a weld between the container boss rim 46 and the cap annular wall or flange 67. The surface of the cap flange 67 that engages the container boss rim 46 may be provided with a small, outwardly projecting, annular energy directing ring 98 (FIGS. 6 and 8–10), and this ring can have a V-shaped transverse cross section for effectively directing the ultrasonic energy at the weld region.

After the cap 12 has been secured by ultrasonic welding to the container, the penetration apertures 84 and 86 lie on opposite sides of the parting line 42 as shown in FIG. 4A. The small ridge of material that is typically defined along, or by, the mold parting plane (along the illustrated parting line 42) is thus located laterally to the side of each of the penetration apertures 84 and 86. Accordingly, if a piercing spike, cannula, or syringe needle is inserted through one of the apertures 84 or 86 to pierce the container end wall membrane 60, then the tip of the spike, cannula, or needle will not impinge upon the parting line 42. The piercing operation is thus more easily effected because the tip of the piercing instrument encounters a generally flat, smooth surface on the container end wall membrane 60 in registry with the aperture 84 or 86.

As illustrated in FIGS. 1, 2, 3, 4A, and 11, the releasable cover 14 may optionally be applied over the end of the cap 12. To this end, the cover 14 is preferably secured, with adhesive or other suitable securing means, to the rim 74 which projects outwardly at the periphery of the cap end wall 72. The cover 14 may be a thin plastic film, paper, foil, or other suitable member. The cover 14 can be coated with adhesive to assist in securing it to the cap 12, and the cover 14 can include a tab to facilitate pulling away the cover 14 when access to the pierceable target regions are desired.

Each of the exposed, pierceable, seal target regions 85 and 87 defined within the cap apertures 84 and 86, respectively, may be provided with a suitable inscription legend or other indicia for identifying the use of that target region or for providing other information. Further, each target region or area 85 and 87 can be molded with a slightly concave surface (not illustrated) to provide a greater structural definition.

Figure 15:
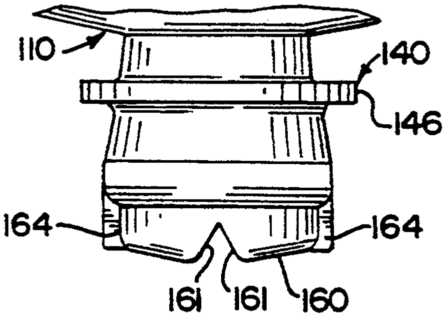
FIG. 15 is a fragmentary, front elevational view of a second embodiment of a container and cap of the present invention, which embodiment includes a recess for receiving a piercing spike.
Figure 16:
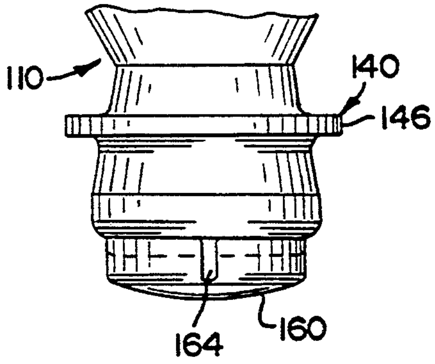
FIG. 16 is a fragmentary, right side elevational view of the structure shown in FIG. 15.
Figure 17:
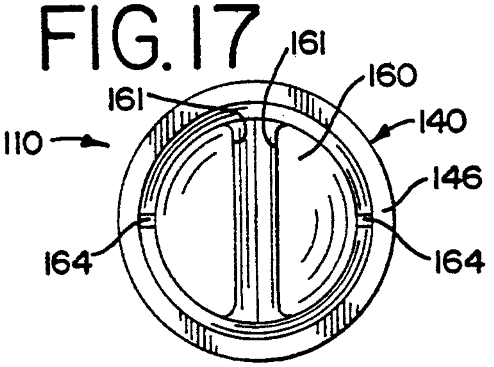
FIG. 17 is a bottom plan view of the structure shown in FIG. 15.

A second embodiment of a container 110 is illustrated in FIGS. 15–17, and the container 110 can have a body portion substantially identical to that of the container 10 described above with reference to FIGS. 1–14. The container 110i has a boss 140 defining a draining sump in communication with the interior of the container 110. The boss 140 can be configured to receive a cap (not illustrated) that is similar or identical to the cap 12 described above with reference to FIGS. 1–14. To this end, the boss 140 includes a rim 146 (to which the cap can be ultrasonically welded) and a pair of orientation lugs 164.

The boss 140 may be also characterized as defining an access port (not visible) which is coextensive with, and sealed by, an end wall or sealing wall 160. The sealing wall 160, or a portion thereof, defines a pierceable membrane for being pierced by an instrument such as a draining spike, cannula, syringe needle, or the like.

The piercing operation is facilitated by providing a novel structure within the sealing wall 160. In the embodiment illustrated in FIGS. 15–17, the sealing wall 160 defines a pair of guide surfaces 161. The guide surfaces 161 each have a generally planar configuration, and the guide surfaces 161 meet to define a generally V-shaped concave recess having a vertex along which the pierceable membrane is defined. Thus, as the piercing instrument is moved against the end wall 160 in the region of the groove defined by the guide surfaces 161, the tip of the piercing instrument will slide along one or the other of the guide surfaces 161 to the vertex or bottom of the configuration and be guided against the pierceable membrane. In a presently contemplated embodiment, the included angle between the two converging surfaces 161 is between about 20° and about 60°.

Figure 18:
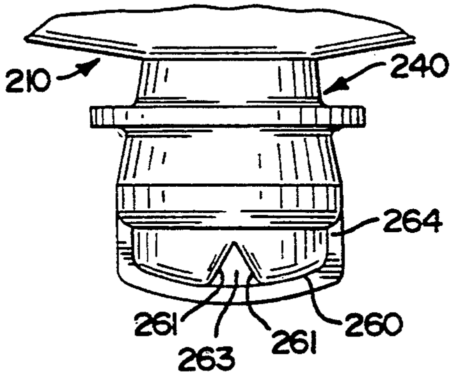
FIG. 18 is a front elevational view of a third embodiment of a container and cap of the present invention, which embodiment includes a modified form of a recess for receiving a piercing spike.
Figure 19:
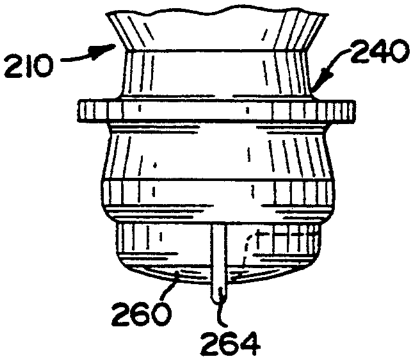
FIG. 19 is a left side elevational view of the structure in FIG. 18.
Figure 20:
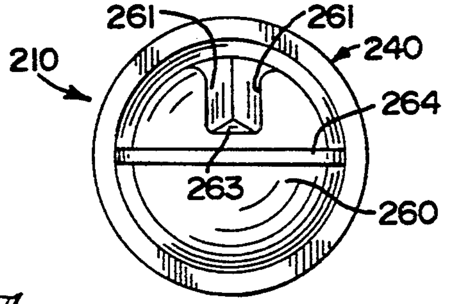
FIG. 20 is a bottom plan view of the structure shown in FIG. 18.

A third embodiment of a container 210 is illustrated in FIGS. 18–20 and is similar to the second embodiment of the container 110 described above with reference to FIGS. 15–17. In the third embodiment, a boss 240 is provided with an orientation wall 264 extending across the top of a sealing wall 260. The peripheral margins of the wall 264 can function in the same manner as the lugs 64 on the first embodiment of the container 10 described above with reference to FIGS. 1–14. Thus, the orientation wall 264 functions to orient a cap, such as the first embodiment cap 12 described above with reference to FIGS. 1–14.

The sealing wall 260, on one side of the orientation wall 264, defines three guide surfaces for accommodating the penetration of a piercing instrument. Two planar guide surfaces 261 define a generally V-shaped concave recess which is open at one end to the peripheral edge of the boss 240 and which is closed at the other end by a generally planar, slanted guide wall 263. The tip of a piercing instrument will be guided by one of the three guide surfaces as it is moved into engagement with the sealing wall 260 so as to facilitate penetration of the membrane defined at the junction of the two walls 261.

Although the illustrated embodiments of the container (10, 110, and 210) are adapted to carry a cap (e.g., cap 12 illustrated in FIGS. 1–14) as part of a dispensing package or system, it will be appreciated that a cap need not be employed in all applications. If it is desired to merely provide a hermetically sealed container that can be drained by puncturing the container and that does not require a reseal capability upon removal of the puncturing instrument, then the cap can be omitted.

The container and package of the present invention can be used in a variety of applications in a number of different ways. The package can be provided in a variety of specific configurations for accommodating particular uses, different piercing instruments, etc.

The package of the present invention is especially suitable for use in dispensing liquids or other substances to a patient. The improved package of the present invention can be readily fabricated in a self-contained configuration by relatively inexpensive, but sterile processes.

It will be readily apparent from the foregoing detailed description of the invention and the illustrated embodiments thereof that numerous other variations and modifications may be effected without departing from the true spirit and scope of the novel concepts or principles of this invention.

What is claimed is:

1. A pierceable, unitary, molded container having a peripheral parting line that delineates opposing portions of the container and comprising:
   a hollow body portion defining an access port and suitable for containing a substance to be drained therefrom;
   a unitary sealing wall coextensive with and sealing said access port;
   a pierceable membrane in said sealing wall; and
   said sealing wall defining guide surfaces that converge toward said pierceable membrane and define to one side of said parting line a recess for receiving a piercing spike means therewith.

2. The container in accordance with claim 1 in which
   said sealing wall defines two of said guide surfaces;
   said guide surfaces each have a generally planar configuration; and
   said guide surfaces meet to define a generally V-shaped concave recess having a vertex along which said pierceable membrane is defined.

3. The container in accordance with claim 2 in which
   said hollow body portion has a boss defining a sump communicating with the interior of said body portion;
   said boss defines said access port; and
   said sealing wall defines an end of said boss.

4. The container in accordance with claim 2 in which said container is filled and hermetically sealed.

5. A sealed but pierceable package comprising:
   a molded container having a peripheral parting line that delineates opposing portions of the container and an access port thereto defined by a boss unitary with said container and sealed by a unitary pierceable membrane;
   a cap secured to said boss over said membrane, said cap including a pierceable, resilient, self-sealing liner juxtaposed over said container membrane; and
   said self-sealing liner including an exposed target surface and a deformable interior surface facing toward said pierceable membrane to one side of said parting line, said deformable interior surface defining a recess aligned with said exposed target surface and providing an inwardly enlarging passageway for a piercing spike while supplying increased resistance against removal of said piercing spike when inserted through said target surface.

6. The package in accordance with claim 5 in which
   said cap has an end wall and a depending peripheral skirt;
   said liner is a thermoplastic polymer rubber that is molded into said cap; and
   said cap end wall defines an aperture providing access to said exposed target surface of said liner.

7. The package in accordance with claim 6 in which
   said enlarging passageway is defined by (1) a first cylindrical recess in said liner aligned with said exposed target surface and (2) a larger diameter second cylindrical recess in said liner that is coaxial with said first recess for providing an annular shoulder around said first recess which supplies increased resistance to removal of a piercing spike that has a diameter less than the diameter of said first recess and that is inserted through said liner in general alignment with said exposed target surface, first recess, and second recess to pierce said membrane.

8. The package in accordance with claim 5 in which said container is filled and hermetically sealed.

9. A pierceable package comprising:
   a molded container having an access port thereto defined by a boss unitary therewith and sealed by a unitary pierceable membrane and having a peripheral parting line that delineates opposing portions of the container;
   a cap mounted on said boss over said membrane and including a pierceable, resilient, self-closing seal in registry over an area of said container membrane to one side of said parting line, said cap including a housing that is substantially more rigid than said seal and that encloses said seal while exposing at least one pierceable target region of the seal, said housing being secured to said container boss to retain said seal in position and including an annular, raised rim around said seal target region; and
   a removable cover releasably sealed to said housing rim over said self-closing seal to isolate said seal target region from the ambient atmosphere.

10. The package in accordance with claim 9 in which said container is filled and hermetically sealed.

11. A pierceable package comprising:
   a molded container with a parting line delineating opposing portions of the molded container, said container having an access port thereto defined by a boss and sealed by a pierceable membrane; and
   a cap for attachment to said boss over said membrane, said cap including a resilient, self-sealing liner having an exposed, pierceable, target portion over said container membrane;
   said container boss and said cap having cooperating orientation means for the placement of said cap on said container boss in a predetermined orientation relative to one another and for positioning said target portion away from said parting line.

12. The package in accordance with claim 11 in which
   said container is molded from thermoplastic material as a unitary structure which is filled and hermetically sealed; and
   said container parting line is defined at least in part by a ridge of said material extending across said membrane.

13. The package in accordance with claim 11 in which
   said parting line extends across part of said membrane;
   one of said cap and container defines a lug; and
   the other of said cap and container defines a recess for engaging said lug when said cap and container are in said predetermined orientation whereby said target portion is displaced from said parting line and is absent from the region between said target portion and said membrane.

14. A molded, filled, and collapsible container from which a substance can be drained under the influence of gravity, said container comprising:

a molded body portion having a sump at one end of said body portion that communicates with the interior of said body portion, said sump including closure means for accommodating draining of said substance therethrough; and said body portion being defined by a pair of opposed walls joined around at least a portion of the periphery of said body, one of said walls being structurally less stiff than the other wall and collapsing inwardly toward the other wall in a generally nesting relationship when said substance is drained from said container.

15. The container in accordance with claim 14 in which both of said walls are flexible; and said one wall is thinner than the other wall.

16. The container in accordance with claim 14 in which said walls define oppositely projecting convex front and rear regions and define oppositely facing concave side edge regions where said walls are joined together.

17. The container in accordance with claim 16 in which the locus of the intersection of each said wall with a first selected plane defining a transverse cross section of said container has a length equal to the length of the locus of the intersection of the wall with a second selected plane parallel to, and spaced from, said first selected plane wherein said planes are longitudinally located to intersect said concave side edge regions.

18. The container in accordance with claim 14 in which said body sump has an access port thereto defined by a boss; and said closure means includes a pierceable membrane sealing said access port.

* * * * *